(12) United States Patent
Baiocchi et al.

(10) Patent No.: US 6,699,841 B2
(45) Date of Patent: Mar. 2, 2004

(54) METHOD OF PREPARING PHYSIOLOGICALLY ACCEPTABLE AQUEOUS SOLUTIONS, AND SOLUTIONS THUS OBTAINED

(76) Inventors: Leandro Baiocchi, Via Belluno, 3, Rome (IT), 00161; Mauro De Gregorio, Via Alessandro Luzio, 18, Rome (IT), 00179

( * ) Notice: Subject to any disclaimer, the term of this patent is extended or adjusted under 35 U.S.C. 154(b) by 0 days.

(21) Appl. No.: 10/058,080

(22) Filed: Jan. 29, 2002

(65) Prior Publication Data

US 2002/0193322 A1 Dec. 19, 2002

(30) Foreign Application Priority Data

Jan. 30, 2001 (IT) ................................. RM2001A0048

(51) Int. Cl.[7] ........................ A01N 43/04; A61K 31/70
(52) U.S. Cl. ........................................... 514/33; 514/35
(58) Field of Search ..................... 514/33, 35

(56) References Cited

U.S. PATENT DOCUMENTS

| | | | |
|---|---|---|---|
| 4,176,228 A | 11/1979 | Hartung .......................... | 536/4 |
| 4,278,657 A | 7/1981 | Tezuka et al. .................. | 424/63 |
| 4,481,187 A | 11/1984 | Kondo et al. ................... | 424/63 |
| 5,183,802 A | 2/1993 | Aliverti et al. ................. | 514/2 |
| 5,238,917 A | 8/1993 | Fujii et al. ...................... | 514/2 |
| 5,459,157 A | 10/1995 | Stroppolo et al. ........... | 514/401 |

FOREIGN PATENT DOCUMENTS

| | | | |
|---|---|---|---|
| JP | 04327533 | * | 11/1992 |
| JP | 08-310953 | * | 11/1996 |
| JP | 09-087201 | * | 3/1997 |
| RU | 2054433 | * | 2/1996 |
| WO | WO 93/06854 | * | 4/1993 |

OTHER PUBLICATIONS

Dolmen—Aspirin with Codeine Effervescent Tablet. Product description from "24/7 Pharmacy" Website (©2001).*
New England Journal of Medicine, vol. 310, pp. 743–746 (1984)—abstract.*
The Merck Index, 13th ed., Merck & Co., Inc. Whitehouse Station, NJ, pp. 11,12,87 and 1542 (2001).*
Patent Abstracts of Japan and Derwent Abstract, XP–002174741, AN 197–255473, JP 9–087201, Mar. 31, 1997.
Derwent Abstract, AN 1999–379840 (32), XP–002174742, JP 11–147825, Jun. 2, 1999.
Chemical Abstract, XP–002174740, JP 9–249694, Sep. 22, 1997.
Derwent Abstract, XP–002174743, AN 1991–226430 (31), JP 3–145432, Jun. 20, 1991.
Patent Abstracts of Japan, JP 3–099023, Apr. 24, 1991.
Patent Abstracts of Japan, JP 10–025255, Jan. 27, 1998.
Patent Abstracts of Japan and Chemical Abstract, AN 113:65296x, JP 2–083318, Mar. 23, 1990.
A. T. Florence, et al., Booknews, Inc., Second Edition, p. 154, "Physicochemical Principles of Pharmacy", Mar. 1988.
S. H. Yalkowsky, Editor, Marcel Dekker, Inc., p. 149 and 151, "Techniques of Solubilization of Drugs", 1981.
C. Runti, Edizioni LINT Trieste, vol. III p. 265, "Fondamenti Di Chimica Farmaceutica", Nov. 1970.
W. Voss, et al., vol. 70, pp. 122 and 129, "Zur Kenntnis Des Glycyrrhizins", 1937.
REFI 3rd Edizione, pp. A–578, A–808, A–646, and A–249, "Repertorio Farmaceutico Italiano", 1989.

* cited by examiner

*Primary Examiner*—Richard L. Raymond
*Assistant Examiner*—Zachary C. Tucker
(74) *Attorney, Agent, or Firm*—Oblon, Spivak, McClelland, Maier & Neustadt, P.C.

(57) ABSTRACT

A physiologically acceptable aqueous solution, and water-soluble compositions suitable for obtaining it, comprising a first physiologically acceptable compound of an acidic nature and a second physiologically acceptable compound of a basic nature that are able to give rise to a precipitate in water, characterized in that it also contains a trisubstituted salt of glycyrrhizic acid in a sufficient quantity to form a clear solution in water.

A method for preparing the said solution.

49 Claims, No Drawings

METHOD OF PREPARING PHYSIOLOGICALLY ACCEPTABLE AQUEOUS SOLUTIONS, AND SOLUTIONS THUS OBTAINED

This application is based on application No. RM2001 A 000048 filed in Italy, the content of which is incorporated hereinto by reference.

The present invention relates to a method of preparing physiologically acceptable aqueous solutions and water-soluble compositions suitable for obtaining them, as well as the solutions and the compositions thus obtained.

More particularly, the present invention relates to physiologically acceptable aqueous solutions and water-soluble compositions suitable for obtaining them, comprising a first physiologically acceptable compound of an acidic nature, a second physiologically acceptable compound of a basic nature and a trisubstituted salt of glycyrrhizic acid.

BACKGROUND OF THE INVENTION

In therapeutic and cosmetic practice, both human and veterinary, use is often made of aqueous solutions containing a carboxylic acid or an organic base, possessing low intrinsic solubility (solubility of the undissociated compound). Their salification (generally with alkali metals or hydrophilic amines of low molecular weight for the acids, and with hydrogen halides or hydrophilic organic acids of low molecular weight, for the bases) is employed to provide them with adequate solubility.

Sometimes it is useful to have aqueous solutions containing at least one carboxylic acid and at least one organic base at the same time. Since solutions with basic pH are needed for the solubilization of weak organic acids, and solutions with acid pH are needed for the solubilization of weak organic bases, such compounds often display a high degree of incompatibility in ordinary aqueous solutions because mutual precipitation occurs on mixing them (see A. T. Florence & D. Attwood "Physiochemical Principles of Pharmacy", II edition, Portland Oreg., 1988, p. 154).

Examples of this behaviour that are well known in the literature are the solutions of acetylsalicylic acid (lysine salt) with chlorpromazine (hydrochloride) or promethazine (hydrochloride) (Repertorio Farmaceutico Italiano 1989 (REFI) page A-578); solutions of furosemide (sodium salt) with organic bases (REFI, page A-808); solutions of dimemorfan (phosphate) with penicillin (sodium salt) or of sodium salicylate (REFI page A-646).

It should be noted, moreover, that the phenomenon is rather more complex than might appear at first sight because, depending on circumstances, there may be precipitation of the acid compound, or of the basic compound, or of a mixture of the two, or of adducts, known as hydrophobic ion pairs. In this last case, which is very common, there may be formation of precipitates, even when one of the two components, for example quaternary ammonium compounds, has good intrinsic solubility.

The incompatibility is more or less pronounced depending on the pK, on the nature and on the intrinsic solubility of the components that determine it. In fact, cases of absolute incompatibility are encountered in practice, in which it is practically impossible to obtain solutions containing the two pharmacologically active compounds at any therapeutically useful concentration, and cases of partial incompatibility in which it is possible to obtain solutions but only in a very restricted range of concentration.

The problem of incompatibility is not solved by separate administration of the solutions of the different pharmacologically active compounds to the patient, unless there is a considerable interval of space and/or time between the applications. Otherwise, in fact, incompatibility between the two pharmacologically active compounds and inactivation occur at the site of actual application (see, for example, the case of cephalosporins and of aminoglycosides (REFI page A-249)). In each case separate application, besides being inconvenient, proves completely impossible in some cases, for example when one of the compounds performs the functions of a preservative.

STATE OF THE ART

In some cases the problem has been solved by using specific pharmaceutical formulations. Thus, the incompatibility between certain carboxylic acids and certain basic decongestants is eliminated by means of a mixture of polysorbates and a polyoxamer (U.S. Pat. No. 5,459,157). Moreover, it should be pointed out that in this case, as in other similar cases, the concentration of these additives is very high (12%) relative to that of the pharmacologically active compounds (0.05–0.1%).

Glycyrrhizic acid, the principal component of the extract of *Glycyrrhiza Glabra,* was isolated by Karrer and Chao and its tricarboxylic acid structure was established by Ruzicka in 1943 (Merck Index, XII ed., 4515). Two epimers of glycyrrhizic acid are known, designated 18α and 18β, but the second is the commonest and it is this that is being referred to whenever the nature of the epimer is not expressly indicated (Runti, Fondamenti di chimica farmaceutica [Fundamentals of pharmaceutical chemistry], Trieste 1969, Vol. III, page 265).

Various salts of glycyrrhizic acid, called glycyrrhizinates, have been described in the literature.

A typical, commercially available monosubstituted salt is the monoammonium salt "Glycamil™" of the company Indena of Milan. Typical disubstituted salts are the dipotassium salt, "Ritamectant K2™" of the R.I.T.A. Corporation, and the mixed salts of potassium, calcium and magnesium called "glycyrrhizines" (U.S. Pat. No. 4,176,228). A typical trisubstituted salt is the tripotassium salt (Voss et al., Ber. 70, 122, 1937).

The monosubstituted and disubstituted salts are widely used in the food and pharmaceutical industry, principally as sweeteners.

Apart from some mild therapeutic activities that have been under investigation for several years (antiulcer activity, anti-AIDS activity, treatment of hepatitis B), certain functions of glycyrrhizic acid and its salts as "adjuvants" in pharmaceutical formulations have also been described from time to time.

The action of "enhancers" of absorption through the skin and the mucous membranes is well documented (U.S. Pat. Nos. 5,183,802; 5,238,917; JP 3099023).

Japanese patent JP 10025255 proposes the use of glycyrrhizic acid, its salts or its esters, for the preparation of solid complexes with antiulcer, anti-inflammatory or antihistaminic drugs for the purpose of improving their absorption (rate of solution). It is known, however, that the complexes that can be used for increasing the rate of solution cannot be used for increasing equilibrium solubility (A. J. Repta in "Technique of Solubilation of Drugs" (S. H. Yalkowsky ed. Marcel Dekker N.Y. 1981 page 135 ff.; pages 149 and 151).

In two Japanese patent documents (Jpn Kokai 0283,318 and JP 3145432A) reference is made to clear solutions containing salts of glycyrrhizic acid, quaternary ammonium compounds and respectively, sodium condoitrinsulphate, borax and taurine in the first case, and lysozime (hydrochloride) in the second. In the first case (C.A. 113, 65296x) the salt used is dipotassium glycyrrhizinate.

U.S. Pat. No. 4,481,187 discloses the use of glycyrrhizic acid or its salts for solubilizing oily substances in water, such as oil-soluble hormones and perfumes.

JP 09 087201 discloses a liquid composition containing acetaminophenone, a saccharide, a salt of glycyrrhizic acid and a glycol. Acetaminophenone, however, is neither acid nor basic in nature. Indeed, it is neutral.

In patents relating to the use of glycyrrhizic acid, generally reference is made to its salts, without differentiating them. However, monosubstituted and disubstituted salts are normally used in the examples given in these documents. Just occasionally, as in U.S. Pat. No. 4,278,657, which proposes the use of glycyrrhizic acid and its salts in synergy with certain polysaccharides as emulsifiers of water and oil mixtures, examples with trisubstituted salts are also given. However, neither this nor other patents describe or claim that the trisubstituted salts have any property at all that is different from the mono- and disubstituted salts.

BRIEF DESCRIPTION OF THE INVENTION

It has now been found, unexpectedly, that the compositions comprising the salt of a first physiologically acceptable compound of an acidic nature and the salt of a second physiologically acceptable compound of a basic nature, which give rise to mutual precipitation in water, can easily be solubilized in water by adding a suitable amount of a trisubstituted salt of glycyrrhizic acid. Naturally, apart from a first physiologically acceptable compound of an acidic nature and a second physiologically acceptable compound of a basic nature, other physiologically acceptable compounds of an acidic and/or basic nature can also be present.

DETAILED DESCRIPTION OF THE INVENTION

In a first aspect, the present invention therefore relates to a method for forming an aqueous solution comprising a first physiologically acceptable compound of an acidic nature and a second physiologically acceptable compound of a basic nature that are able to give rise to a precipitate in water, characterized in that a trisubstituted salt of glycyrrhizic acid is added in sufficient quantity to form a clear solution.

In a second aspect, the present invention relates to a physiologically acceptable aqueous solution comprising a first physiologically acceptable compound of an acidic nature and a second physiologically acceptable compound of a basic nature that are able to give rise to a precipitate in water, characterized in that it also includes a trisubstituted salt of glycyrrhizic acid in sufficient quantity to form a clear solution.

Moreover, in a further aspect, the present invention relates to a composition comprising a first physiologically acceptable compound of an acidic nature and a second physiologically acceptable compound of a basic nature that are able to give rise to a precipitate in water, characterized in that it also includes a trisubstituted salt of glycyrrhizic acid in sufficient quantity to form a clear solution when the said composition is added to water.

For the purposes of the present invention, the glycyrrhizic acid can be either in the form of epimer 18α or of epimer 18β. The latter is preferred, however, because it is more readily available commercially.

The cation of the trisubstituted salt of glycyrrhizic acid according to the present invention can be any physiologically acceptable, organic or inorganic cation, for example sodium, potassium, ammonium, calcium, magnesium, monoethanolamine, diethanolamine, triethanolamine, lysine, arginine, tromethamine and the like. There is no limitation on the use of mixed trisubstituted salts.

Solutions of disodium monoammonium glycyrrhizinate obtained by neutralizing the commercial ammonium monoglycyrrhizinate with the required quantity of aqueous solution of sodium hydroxide are easily accessible and particularly advantageous. For example, with a 0.2 N solution of sodium hydroxide it is easy to obtain a solution of disodium monoammonium glycyrrhizinate at concentrations above 8%, the exact value depending on the strength of the commercial ammonium glycyrrhizinate used. Naturally, neutralization can also be carried out, as well as with sodium hydroxide, with potassium hydroxide, with ethanolamine, with diethanolamine, with ammonia or with their obvious equivalents.

Because the absolute concentration and the proportions between the components in the composition of the invention are not determined by stoichiometric requirements but by therapeutic or pharmaceutical requirements and because the phenomenon of mutual precipitation is governed by the nature of the components, there is not an optimum concentration of trisubstituted glycyrrhizinate that can be used in all cases.

However, it is very easy to identify it in any individual instance by mixing together, with vigorous stirring in water, a salt of a first physiologically acceptable compound of an acidic nature and a neutral salt of a second physiologically acceptable compound of a basic nature that are able to give rise to a precipitate in water, at the concentration and in the proportions that are predetermined by therapeutic, pharmaceutical, cosmetic or similar requirements. Then an aqueous solution of a trisubstituted glycyrrhizinate is added gradually, in portions, to the suspension that forms, until a clear solution is obtained. Preferably, the total amount of water is preselected so that at the end of the operation the total volume is reasonably lower (5–10%) than the required final volume and then it is made up to volume with water. Advantageously, the aqueous solution of glycyrrhizinate is added very slowly and with vigorous stirring. In fact, attainment of equilibrium in a few hours is by no means rare.

The amount of trisubstituted glycyrrhizinate required to achieve solubilization of the precipitates varies, in the examples given further on, between 0.27 and 2.7% (concentrations expressed as disodium ammonium glycyrrhizinate). However, for the reasons previously presented concerning the nature of the phenomena involved and the factors affecting them, a person skilled in the art will easily understand that the amount of trisubstituted glycyrrhizinate required could, in a particular case, also undergo reasonable deviations, higher or lower relative to the aforesaid range, while remaining within the scope of the present invention.

Having thus easily determined in the laboratory the appropriate quantity of trisubstituted glycyrrhizinate required for the particular composition under consideration, large-scale preparation of the solutions of the invention will preferably be effected by mixing together, in the desired order, the predetermined quantities of the various components as solids or as solutions.

For example, the following are added, in this order, to a preselected quantity of water:

a quantity of a base (for example sodium hydroxide, potassium hydroxide, ethanolamine, diethanolamine, triethanolamine, tromethamine, lysine, arginine, or sodium bicarbonate) sufficient to salify either the two free carboxyls of the predetermined quantity of ammonium glycyrrhizinate, or the preselected quantity of a physiologically acceptable compound of an acidic nature if the latter is used as free acid as well as salt;

the said physiologically acceptable compound of an acidic nature the monoammonium glycyrrhizinate, and the preselected quantity of a neutral salt of a physiologically acceptable base.

If the salt of the physiologically acceptable base is an acid salt, for example the sulphate or those of dicarboxylic acids, due account of it is taken by suitably increasing the initial quantity of base. Similarly, the quantity of base used will be reduced whenever the physiologically acceptable base is used in the free form as well as in the form of salt.

So far, no appreciable drawback has been observed when using an excess of trisubstituted glycyrrhizinate, relative to the minimum quantity required for obtaining a clear solution. Indeed, an improvement in stability of the solution has been observed in some cases.

The compositions of the invention could also be in the form of powders for dissolving or as concentrated solutions for diluting in water, or in aqueous liquids, at the time of use. Forms that could be used for this purpose are granules, freeze-dried products, tablets and the like, produced by traditional galenical techniques, well known to a person skilled in the art, comprising simple operations such as granulation, tableting, dissolving, sterilizing, freeze-drying etc.

Preferably, the physiologically acceptable compound of an acidic nature according to the present invention is a carboxylic acid.

In its turn, the physiologically acceptable compound of a basic nature according to the present invention is, preferably, an organic base.

The physiologically acceptable compounds that are preferred according to the present invention are those that display a therapeutically useful pharmacological or pharmaceutical activity.

The physiologically acceptable compounds of an acidic nature, characterized in that the aqueous solutions of their salts (with alkali metals and alkaline earth metals, ammonium, hydroxyamines, basic amino acids, tromethamine etc.) are incompatible with aqueous solutions of salts of organic bases, and belong to various chemical therapeutic categories.

A typical example of a first important class of these compounds comprises the non-steroidal anti-inflammatory drugs (NSAIDs). Typical examples of NSAIDs are arylalkanoic acids (ketoprofen, napoxen, ibuprofen, flurbiprofen, diclofenac, sulindac and the like), anthranilic acids (mefenamic acid, flufenamic acid and the like), salicylic acids (aspirin, diflunisal and the like), and some heterocyclic acids (indometacin, flunoxaprofen, ketorolac).

A typical example of a second class comprises diuretics such as ethacrynic acid, furosemide and the like.

A typical example of a third class comprises anti-allergic drugs such as lodoxamide, tranilast and their analogues.

A typical example of a fourth class comprises the 21-phosphoric and 21-hemisuccinic esters of corticosteroids.

Further examples of therapeutically useful compounds of an acidic nature characterized by the fact that aqueous solutions of their salts are incompatible with aqueous solutions of salts of organic bases are carboxylic acids belonging to other therapeutic classes such as: aryloxy-alkanoic acids, sorbic acid, pirfenoxone, folic acid, fusidic acid, theophylline-acetic acid, bendazac, prostaglandins, ACE inhibitors, penicillins, cephalosporins, quinolonics and the like.

The physiologically acceptable compounds of a basic nature, characterized in that the aqueous solutions of their salts (with hydrogen halides, sulphuric acid, phosphoric acid, nitric acid, low molecular weight organic acids, hydroxylates and/or polycarboxylic acids and the like) are incompatible with aqueous solutions of salts of organic acids, and these too belong to various chemical and therapeutic classes.

A typical example of a first class of such compounds comprises antihistamines such as: chlorpheniramine, promethazine, azelastine, antazoline, cyproheptadine, tonzylamine, diphenhydramine, emedastine, ketotifen and the like.

A typical example of a second class comprises mucolytics such as: ambroxol, bromexine and the like.

A typical example of a third class comprises vasoconstrictors such as: naphazoline, tetryzoline, tramazoline and the like.

A typical example of a fourth class comprises β-blockers such as: timolol, carteolol and the like.

A typical example of a fifth class comprises antispasmodics such as: ipratropium bromide, octylonium bromide and the like, papaverine, rociverine, toripramide and the like.

A typical example of a sixth class comprises antiseptics such as: chlorhexidine, benzalkonium chloride, benzetonium chloride, benzoxonium chloride, dequalinium chloride and the like.

A typical example of a seventh class comprises antitussives such as: codeine and codeine-like drugs, oxolamine, dimemorfan, cloperastine.

A typical example of an eighth class comprises basic anti-inflammatory drugs such as: benzydamine and the like.

A typical example of a ninth class comprises bronchodilators such as: salbutamol, fenspiride and the like.

A typical example of a tenth class comprises sympathicolytics such as: dapiprazole, prazosin, chlorpromazine and the like.

Further examples of therapeutically useful compounds of a basic nature belong to other classes such as central analgesics, antibiotics, fluoroquinolones and the like.

The compounds of the invention can also contain other traditional types of ingredients such as pH adjusters, antioxidants, stabilizers, preservatives, viscosity enhancers, chelating agents, humectants, colouring matter, substances for achieving isotonia, etc. With regard to isotonia, no macroscopic effects due to the concentration of sodium chloride in the solutions are known.

A person skilled in the art will be able to introduce many variants (such as various salts), without departing from the spirit of the present invention, according to the nature and quantity of the physiologically acceptable compounds used and the type of final composition to be obtained.

For example, the compound having acidic nature and the compound having basic nature may be a polymer such as xanthan gum, carboxymethyl cellulose, chitosan and the like.

EXAMPLE 1

Solution of diclofenac, tetryzoline and benzalkonium chloride

A) PREPARATION OF THE "GLY SOLUTION"

94.4 ml of a 0.2 N solution of NaOH was added to 8.44 g of monoammonium glycyrrhizinate trihydrate. The resulting solution was brought up to the volume (100 ml) with distilled water. A solution with 8.34% of disodium monoammonium glycyrrhizinate ($GlyNH_3Na_2$) was thus obtained, and will be designated as "Gly solution" hereinafter.

B) PREPARATION OF A SOLUTION OF DICLOFENAC, TETRYZOLINE AND BENZALKONIUM CHLORIDE

The following were added, in this order, with stirring, to 40 ml of water:

10 ml of aqueous solution of diclofenac sodium salt at 1%

50 mg of tetryzoline hydrochloride 2 ml of aqueous solution of benzalkonium chloride at 0.5%

The "Gly solution" was added in portions of approx. 1 ml to the milky suspension, with a few minutes between each addition, obtaining complete solubilization after addition of 14.5 ml. The solution thus obtained was made up to 100 ml with distilled water. Final composition:

| | |
|---|---|
| diclofenac sodium salt | 100 mg |
| tetryzoline hydrochloride | 50 mg |
| benzalkonium chloride | 10 mg |
| $GlyNH_3Na_2$ (14.5 ml of "Gly solution") | 1.2 g |
| Water, sufficient for: | 100 ml |

EXAMPLE 2

Solution of ibuprofen and chlorpromazine

An aqueous solution containing 0.63 g of ibuprofen and 15.3 ml of 0.2 N NaOH in a volume of 40 ml was prepared. Then a similar procedure was followed to that described in Example 1 above, obtaining a solution having the following composition:

| | |
|---|---|
| Ibuprofen | 0.63 g |
| NaOH (0.2 N: 15.3 ml) | 123 mg |
| chlorpromazine hydrochloride | 0.70 g |
| $GlyNH_3Na_2$ (22.8 ml of "Gly solution") | 1.90 g |
| water, sufficient for: | 100 ml |

EXAMPLE 3

Solution of ibuprofen and benzoxonium chloride

Following a similar procedure to that described in Example 2 above, a solution was prepared having the following composition:

| | |
|---|---|
| ibuprofen | 0.70 g |
| NaOH (0.2 N: 17 ml) | 136 mg |
| benzoxonium chloride | 70 mg |
| $GlyNH_3Na_2$ (13.8 ml of "Gly solution") | 1.15 g |
| water, sufficient for: | 100 ml |

EXAMPLE 4

Solution of ketoprofen, chlorhexidine and benzalkonium chloride

Following a procedure similar to that described in Example 2 above, a solution was prepared having the following composition:

| | |
|---|---|
| ketoprofen | 0.50 g |
| NaOH (0.2 N: 9.85 ml) | 79 mg |
| chlorhexidine digluconate | 0.10 g |
| benzalkonium chloride | 0.10 g |
| $GlyNH_3Na_2$ (18 ml of "Gly solution") | 1.50 g |
| water, sufficient for: | 100 ml |

EXAMPLE 5

Solution of naproxen and chlorpheniramine

Bearing in mind, in the calculations of the quantity of alkali required for also neutralizing the free carboxyl of the maleic acid in the chlorpheniramine maleate, 0.5 g of naproxen and 0.4 g of chlorpheniramine maleate were added, in that order, to 40 ml of an aqueous solution containing 16 ml of NaOH 0.2 N. The milky suspension became clear on adding, with stirring, 3.2 ml of "Gly solution". Solution composition:

| | |
|---|---|
| naproxen | 0.50 g |
| NaOH (0.2 N: 16 ml) | 128 mg |
| chlorpheniramine maleate | 0.40 g |
| $GlyNH_3Na_2$ (3.2 ml of "Gly solution") | 0.27 g |
| water, sufficient for: | 100 ml |

EXAMPLE 6

Solution of furosemide and timolol

Following a procedure similar to that described in Example 5 above, a solution was prepared having the following composition:

| | |
|---|---|
| furosemide sodium salt | 0.89 g |
| NaOH (0.2 N: 10.3 ml) | 82 mg |
| timolol maleate | 0.89 g |
| $GlyNH_3Na_2$ (12 ml of "Gly solution") | 1.00 g |
| water, sufficient for: | 100 ml |

EXAMPLE 7

Solution of ketoprofen and chlorpheniramine

The following were added, in the order stated, with stirring and at room temperature, to 90 ml of water:

| | |
|---|---|
| diethanolamine | 0.72 g |
| ketoprofen | 1.00 g |
| monoammonium glycyrrhizinate trihydrate | 1.00 g |
| chlorpheniramine maleate | 0.30 g |

Each component was added when all the preceding components had dissolved. It was made up to 100 ml with distilled water.

EXAMPLE 8

Solution of betamethasone 21-phosphate and ambroxol

The various ingredients were added, with stirring and at room temperature, to 90 ml of water, obtaining a solution having the following composition:

| | |
|---|---|
| betamethasone 21-phosphate disodium salt | 0.15 g |
| ambroxol hydrochloride | 0.27 g |
| monoammonium glycyrrhizinate trihydrate | 0.35 g |
| sodium bicarbonate | 0.07 g |
| water, sufficient for: | 100 ml |

EXAMPLE 9

Solution of naphazoline and diclofenac

The various ingredients were added in the order stated, with stirring and at room temperature, to 90 ml of water, obtaining a solution having the following composition:

| | |
|---|---|
| diclofenac sodium salt | 0.10 g |
| tripotassium glycyrrhizinate | 1.70 g |
| naphazoline hydrochloride | 0.10 g |
| water, sufficient for: | 100 ml |

EXAMPLE 10

Solution of ketoprofen, chlorpheniramine, chlorhexidine and benzalkonium chloride 4.0 g of ammonium glycyrrhizinate trihydrate and 2.0 g of ketoprofen are dissolved in 90 ml of NaOH 0.2 N. Add 0.2 g of hydroxyethyl cellulose dissolved in 20 ml of lukewarm water, then, in this order: 1.0 g of chlorpheniramine maleate, 10 ml of 2% solution of chlorhexidine digluconate, 40 ml of 0.5% benzalkonium chloride and make up to 200 ml with distilled water. The solution thus obtained contains:

| | |
|---|---|
| ketoprofen | 1.00 g |
| monoammonium glycyrrhizinate trihydrate | 2.00 g |
| chlorpheniramine maleate | 0.50 g |
| chlorhexidine digluconate | 0.10 g |
| benzalkonium chloride | 0.10 g |
| NaOH | 0.39 g |
| hydroxyethylcellulose | 0.10 g |
| water, sufficient for: | 100 ml |

EXAMPLE 11

Solution of ketoprofen and chlorpheniramine maleate

The following were mixed in a 10 ml flask:

| | |
|---|---|
| ketoprofen | 1.00 g |
| chlorpheniramine maleate | 0.30 g |
| monoammonium glycyrrhizinate trihydrate | 1.00 g |
| sodium bicarbonate | 0.65 g | all in the form of solids. After homogenization for 15 minutes in a mortar, the mixture proved to be perfectly soluble in 100 ml of drinking water.

EXAMPLE 12

Solution of ketoprofen and promethazine (neutralization of the acids in situ)

1 g of promethazine hydrochloride and then 2.7 g of monoammonium glycyrrhizinate trihydrate (3.02 $10^{-3}$ mol, 6.04 $10^{-3}$ acid equivalents) were added to an aqueous solution obtained by dissolving 1.00 g of ketoprofen (3.93 $10^{-3}$ mol) in 39.3 ml of NaOH 0.1 N (3.93 $10^{-3}$ mol) and then diluting with distilled water to 60 ml. After 2 h with stirring at room temperature, there were still undissolved transparent crystals. 15.1 ml of NaOH 0.2 N (3.02 $10^{-3}$ mol) was added, and the suspension was left, with stirring. After 2 h the solution was still cloudy and contained undissolved crystals. A further 15.1 ml of NaOH 0.2 N (3.02 $10^{-3}$ mol) was added, and a completely clear solution was obtained.

EXAMPLE 13

Solution of ketoprofen and ambroxol

Following a procedure similar to that described in Example 2 above, a solution having the following composition was prepared:

| | |
|---|---|
| ketoprofen | 500 mg |
| NaOH (0.2 N: 9.85 ml) | 79 mg |
| ambroxol hydrochloride | 360 mg |
| GlyNH$_3$Na$_2$ (24 ml of "Gly solution") | 2.0 g |
| water, sufficient for: | 100 ml |

EXAMPLE 14

Solution of ketoprofen and ambroxol

Following a procedure similar to that described in Example 2 above, and adding sodium chloride at the end, a solution having the following composition was prepared:

| | |
|---|---|
| ketoprofen | 0.50 g |
| NaOH (0.2 N: 9.85 ml) | 79 mg |
| ambroxol hydrochloride | 0.36 g |
| GlyNH$_3$Na$_2$ (24 ml of "Gly solution") | 2.0 g |
| NaCl | 0.9 g |
| water, sufficient for: | 100 ml |

EXAMPLE 15

Solution of ketoprofen and ambroxol (use of ambroxol base)

Referring to Example 13, the following are suspended in 40 ml of an aqueous solution containing 46 mg of NaOH (5.8 ml of NaOH 0.2 N). 0.5 g of ketoprofen, 0.33 g of ambroxol base. Then 26.4 ml of "Gly solution" was added. After 45 min of vigorous stirring, a solution was obtained, which was made up to 100 ml with distilled water. Its composition was:

| | |
|---|---|
| ketoprofen | 0.5 g |
| NaOH (0.2 N: 5.8 ml) | 46 mg |
| ambroxol base | 0.33 g |
| GlyNH$_3$Na$_2$ (24 ml of "Gly solution") | 2.0 g |
| water, sufficient for: | 100 ml |

EXAMPLE 16

Solution of diclofenac, chlorpheniramine and benzalkonium chloride

To 40 ml of water, add 6.3 ml of a solution obtained by dissolving 4 g of ammonium glycyrrhizinate pentahydrate in 43 ml of NaOH 0.2 N and make up to 50 ml with distilled water (solution with 8% of ammonium glycyrrhizinate pentahydrate and 7.6% of GlyNH$_3$Na$_2$). The following are then added, in this order:

3.8 ml of NaOH 0.2 N, 10 ml of an aqueous solution of diclofenac sodium salt at 1%, 0.3 g of chlorpheniramine maleate, 2 ml of aqueous solution of benzalkonium chloride at 0.5% and 0.76 g of sodium chloride. It was diluted to 100 ml with distilled water. The composition of the solution was:

| | |
|---|---|
| diclofenac sodium salt | 0.10 g |
| chlorpheniramine maleate | 0.30 g |
| benzalkonium chloride | 0.01 g |
| GlyNH$_3$Na$_2$ | 0.48 g |
| NaOH (3.8 ml: 0.2 N) | 0.03 g |
| NaCl | 0.76 g |
| Water, sufficient for: | 100 ml |

EXAMPLE 17

Solution of diclofenac, chlorpheniramine, tetryzoline and benzalkonium chloride

Following a procedure similar to that described in Example 16 above, a formulation was prepared with the following composition:

| | |
|---|---|
| diclofenac sodium salt | 0.10 g |
| chlorpheniramine maleate | 0.30 g |
| tetryzoline hydrochloride | 0.05 g |
| benzalkonium chloride | 0.01 g |
| GlyNH$_3$Na$_2$ | 0.41 g |
| NaOH (3.8 ml: 0.2 N) | 0.03 g |
| NaCl | 0.76 g |
| Water, sufficient for: | 100 ml |

EXAMPLE 18

Solution of diclofenac, chlorpheniramine and tetryzoline

Following a procedure similar to that described in Example 16 above, a formulation was prepared with the following composition:

| | |
|---|---|
| diclofenac sodium salt | 0.10 g |
| chlorpheniramine maleate | 0.30 g |
| tetryzoline hydrochloride | 0.05 g |
| GlyNH$_3$Na$_2$ | 0.40 g |
| NaOH (3.8 ml: 0.2 N) | 0.03 g |
| NaCl | 0.76 g |
| Water, sufficient for: | 100 ml |

EXAMPLE 19

Solution of diclofenac and lomefloxacin

Taking into account the remarks made regarding Example 5 above and following a similar procedure, a solution was obtained with the following composition:

| | |
|---|---|
| diclofenac sodium salt | 0.10 g |
| lomefloxacin hydrochloride | 0.30 g |
| NaOH (7.8 ml 0.1 N) | 31 mg |
| GlyNH$_3$Na$_2$ | 2.53 g |
| water, sufficient for: | 100 ml |

What is claimed is:

1. A method of forming an aqueous solution comprising
    a first physiologically acceptable compound of an acidic nature, and
    a second physiologically acceptable compound of a basic nature, in a ratio which gives rise to a precipitate in water,
    characterized in that a glycyrrhizic acid tricarboxylate salt is added in sufficient quantity to form a clear solution.

2. The method of claim 1, wherein the cations of the glycyrrhizic acid tricarboxylate salt are selected from the group consisting of sodium, potassium, ammonium, calcium, magnesium, monoethanolamine, diethanolamine, triethanolamine, lysine, arginine, and tromethamine; or a mixture of two or more of said cations.

3. The method of claim 2, wherein the glycyrrhizic acid tricarboxylate salt is monoammonium disodium glycyrrhizinate.

4. The method of claim 1, wherein a base is added in sufficient quantity to ensure salification of the physiologically acceptable compound of an acidic nature.

5. The method of claim 1, wherein the physiologically acceptable compound of an acidic nature is a carboxylic acid.

6. The method of claim 1, wherein the physiologically acceptable compound of a basic nature is an organic base.

7. The method of claim 1, wherein both the physiologically acceptable compound of an acidic nature and that of a basic nature possess a therapeutically useful pharmacological activity.

8. A method of forming an aqueous solution comprising
    a first physiologically acceptable compound of an acidic nature, and
    a second physiologically acceptable compound of a basic nature, in a ratio which gives rise to a precipitate in water,
    characterized in that a glycyrrhizic acid tricarboxylate salt is added in sufficient quantity to form a clear solution,
    wherein both the physiologically acceptable compound of an acidic nature and that of a basic nature possess a therapeutically useful pharmacological activity, and wherein the therapeutically useful compound of an acidic nature is selected from the group consisting of non-steroidal anti-inflammatory drugs, diuretics, antiallergic drugs, 21-phosphoric and 21-hemisuccinic esters of corticosteroids, prostaglandins, ACE inhibitors, penicillins, cephalosporins and fluoroquinolones.

9. A method of forming an aqueous solution comprising
a first physiologically acceptable compound of an acidic nature, and
a second physiologically acceptable compound of a basic nature, in a ratio which gives rise to a precipitate in water,
characterized in that a glycyrrhizic acid tricarboxylate salt is added in sufficient quantity to form a clear solution,
wherein both the physiologically acceptable compound of an acidic nature and that of a basic nature possess a therapeutically useful pharmacological activity, and
wherein the therapeutically useful compound of an acidic nature is selected from the group consisting of ketoprofen, napoxen, ibuprofen, flubiprofen, diclofenac, sulindac, mefenamic acid, flufenamic acid, aspirin, diflunisal, indometacin, flunoxaprofen, ketorolac, ethacrynic acid, furosemide, lodoxamide, tranilast, 21-phosphoric and 21-hemisuccinic esters of corticosteroids, sorbic acid, pirfenoxone, folic acid, fusidic acid, theophylline-acetic acid and bendazac.

10. The method of claim 7, wherein the therapeutically useful compound of a basic nature is selected from the group consisting of antihistamines, mucolytics, vasoconstrictors, β-blockers, antispasmodics, antiseptics, antitussives, basic anti-inflammatory drugs, bronchodilators, sympathicolytics, analgesics and antibiotics.

11. A method of forming an aqueous solution comprising
a first physiologically acceptable compound of an acidic nature, and
a second physiologically acceptable compound of a basic nature, in a ratio which gives rise to a precipitate in water,
characterized in that a glycyrrhizic acid tricarboxylate salt is added in sufficient quantity to form a clear solution,
wherein both the physiologically acceptable compound of an acidic nature and that of a basic nature possess a therapeutically useful pharmacological activity, and
wherein the therapeutically useful compound of a basic nature is selected from the group consisting of chlorpheniramine, promethazine, azelastine, antazoline, cyproheptadine, tonzylamine, diphenydramine, emedastine, ketotifen, ambroxol, bromexine, naphazoline, tetryzoline, tramazoline, timolol, carteolol, ipratropium bromide, octylonium bromide, papaverine, rociverine, toripamide, chlorhexidine, benzalkonium chloride, benzetonium chloride, benzoxonium chloride, dequalinium chloride, codeine, oxolamine, dimemorfan, cloperastine, benzydamine, salbutamol, fenspiride, dapiprazole, chlorpromazine, prazosin, and lomefloxacin.

12. A pharmacologically acceptable solution comprising:
water
a first physiologically acceptable compound of an acidic nature and
a second physiologically acceptable compound of a basic nature
in a ratio which gives rise to a precipitate,
said solution further comprising a glycyrrhizic acid tricarboxylate salt,
wherein said glycyrrhizic acid tricarboxylic salt is present in sufficient quantity to form a clear solution.

13. The composition of claim 12, wherein the cations of the glycyrrhizic acid tricarboxylate salt are selected from the group consisting of sodium, potassium, ammonium, calcium, magnesium, monoethanolamine, diethanolamine, triethanolamine, lysine, arginine, and tromethamine; or mixtures of two or more of said cations.

14. The composition of claim 12, wherein the salt of glycyrrhizic acid is disodium monoammonium glycyrrhizinate obtained by neutralizing commercial monoammonium glycyrrhizinate with a sodium hydroxide solution.

15. The composition of claim 12, wherein the physiologically acceptable compound of an acidic nature is a carboxylic acid.

16. The composition of claim 12, wherein the physiologically acceptable compound of a basic nature is an organic base.

17. The composition of claim 12, wherein both the physiologically acceptable compound of an acidic nature and that of a basic nature possess a therapeutically useful pharmacological activity.

18. The composition of claim 17, characterized in that the therapeutically useful compound of an acidic nature is selected from the group comprising non-steroidal anti-inflammatory drugs, diuretics, anti-allergic drugs, 21-phosphoric and 21-hemisuccinic esters of corticosteroids, prostaglandins, ACE inhibitors, penicillins, cephalosporins and fluoroquinolones.

19. The composition of claim 17, wherein the therapeutically useful compound of an acidic nature is selected from the group consisting of ketoprofen, napoxen, ibuprofen, flurbiprofen, diclofenac, sulindac, mefenamic acid, flufenamic acid, aspirin, diflunisal, indometacin, flunoxaprofen, ketorolac, ethacrynic acid, furosemide, lodoxamide, tranilast, 21-phosphoric and 21-hemisuccinic esters of corticosteroids, sorbic acid, pirfenoxone, folic acid, fusidic acid, theophylline-acetic acid and bendazac.

20. The composition of claim 17, wherein the therapeutically useful compound of a basic nature is selected from the group consisting of antihistamines, mucolytics, vasoconstrictors, β-blockers, antispasmodics, antiseptics, antitussives, basic anti-inflammatory drugs, bronchodilators, sympathicolytics, analgesics and antibiotics.

21. The composition of claim 17, wherein the therapeutically useful compound of a basic nature is selected from the group consisting of chlorpheniramine, promethazine, azelastine, antazoline, cyproheptadine, tonzylamine, diphenydramine, emedastine, ketotifen, ambroxol, bromexine, naphazoline, tetryzoline, tramazoline, timolol, carteolol, ipratropium bromide, octylonium bromide, papaverine, rociverine, toripamide, chlorhexidine, benzalkonium chloride, benzetonium chloride, benzoxonium chloride, dequalinium chloride, codeine, oxolamine, dimemorfan, cloperastine, benzydamine, salbutamol, fienspiride, dapiprazole, chlorpromazine, prazosin, and lomefloxacin.

22. A method for dissolving a precipitate in an aqueous solution comprising:
adding a glycyrrhizic acid tricarboxylate salt to an aqueous solution comprising a precipitate until said precipitate dissolves,
wherein said precipitate has been formed by the combination of a physiologically acceptable compound of an acidic nature with a physiologically acceptable compound of a basic nature and wherein the addition of said glycyrrhizic acid tricarboxylate salt causes said precipitate to dissolve.

23. The method of claim 22, wherein the quantity of said glycyrrhizic acid tricarboxylate salt ranges from 0.27 to 2.7% based on the weight of the solution.

24. The method of claim 22, wherein the cations of the glycyrrhizic acid tricarboxylate salt are selected from the group consisting of sodium, potassium, ammonium, calcium, magnesium, monoethanolamine, diethanolamine, triethanolamine, lysine, arginine, and tromethamine; or a mixture of two or more of said cations.

25. The method of claim 22, wherein the glycyrrhizic acid tricarboxylate salt is monoammonium disodium glycyrrhizinate.

26. The method of claim 22, wherein a base is added in sufficient quantity to ensure salification of the physiologically acceptable compound of an acidic nature.

27. The method of claim 22, wherein the physiologically acceptable compound of an acidic nature is a carboxylic acid.

28. The method of claim 22, wherein the physiologically acceptable compound of a basic nature is an organic base.

29. The method of claim 22, wherein both the physiologically acceptable compound of an acidic nature and that of a basic nature possess a therapeutically useful pharmacological activity.

30. The method of claim 22, wherein the therapeutically useful compound of an acidic nature is selected from the group consisting of non-steroidal anti-inflammatory drugs, diuretics, antiallergic drugs, 21-phosphoric and 21-hemisuccinic esters of corticosteroids, prostaglandins, ACE inhibitors, penicillins, cephalosporins and fluoroquinolones.

31. The method of claim 22, wherein the therapeutically useful compound of an acidic nature is selected from the group consisting of ketoprofen, napoxen, ibuprofen, flubiprofen, diclofenac, sulindac, mefenamic acid, flufenamic acid, aspirin, diflunisal, indometacin, flunoxaprofen, ketorolac, ethacrynic acid, furosemide, lodoxamide, tranilast, 21-phosphoric and 21-hemisuccinic esters of corticosteroids, sorbic acid, pirfenoxone, folic acid, fusidic acid, theophylline-acetic acid and bendazac.

32. The method of claim 22, wherein the therapeutically useful compound of a basic nature is selected from the group consisting of antihistamines, mucolytics, vasoconstrictors, β-blockers, antispasmodics, antiseptics, antitussives, basic anti-inflammatory drugs, bronchodilators, sympathicolytics, analgesics and antibiotics.

33. The method of claim 22, wherein the therapeutically useful compound of a basic nature is selected from the group consisting of chlorpheniramine, promethazine, azelastine, antazoline, cyproheptadine, tonzylamine, diphenydramine, emedastine, ketotifen, ambroxol, bromexine, naphazoline, tetryzoline, tramazoline, timolol, carteolol, ipratropium bromide, octylonium bromide, papaverine, rociverine, toripamide, chlorhexidine, benzalkonium chloride, benzetonium chloride, benzoxonium chloride, dequalinium chloride, codeine, oxolamine, dimemorfan, cloperastine, benzydamine, salbutamol, fenspiride, dapiprazole, chlorpromazine, prazosin, and lomefloxacin.

34. A method for preventing a precipitate from forming in an aqueous solution comprising a physiologically acceptable compound of an acid nature with a physiologically acceptable compound of a basic nature, comprising:
formulating said aqueous solution with an amount of a glycyrrhizic acid tricarboxylate salt sufficient to prevent the formation of a precipitate,
wherein the combination of a physiologically acceptable compound of an acidic nature with a physiologically acceptable compound of a basic nature would otherwise form a precipitate and
wherein the formulation of said aqueous solution with a glycyrrhizic acid tricarboxylate salt prevents the formation of said precipitate.

35. The method of claim 34, wherein the quantity of said glycyrrhizic acid tricarboxylate salt ranges from 0.27 to 2.7% based on the weight of the solution.

36. The method of claim 34, wherein the cations of the glycyrrhizic acid tricarboxylate salt are selected from the group consisting of sodium, potassium, ammonium, calcium, magnesium, monoethanolamine, diethanolamine, triethanolamine, lysine, arginine, and tromethamine; or a mixture of two or more of said cations.

37. The method of claim 34, wherein the glycyrrhizic acid tricarboxylate salt is monoammonium disodium glycyrrhizinate.

38. The method of claim 34, wherein a base is added in sufficient quantity to ensure salification of the physiologically acceptable compound of an acidic nature.

39. The method of claim 34, wherein the physiologically acceptable compound of an acidic nature is a carboxylic acid.

40. The method of claim 34, wherein the physiologically acceptable compound of a basic nature is an organic base.

41. The method of claim 34, wherein both the physiologically acceptable compound of an acidic nature and that of a basic nature possess a therapeutically useful pharmacological activity.

42. The method of claim 34, wherein the therapeutically useful compound of an acidic nature is selected from the group consisting of non-steroidal anti-inflammatory drugs, diuretics, antiallergic drugs, 21-phosphoric and 21—hemisuccinic esters of corticosteroids, prostaglandins, ACE inhibitors, penicillins, cephalosporins and fluoroquinolones.

43. The method of claim 34, wherein the therapeutically useful compound of an acidic nature is selected from the group consisting of ketoprofen, napoxen, ibuprofen, flubiprofen, diclofenac, sulindac, mefenamic acid, flufenamic acid, aspirin, diflunisal, indometacin, flunoxaprofen, ketorolac, ethacrynic acid, furosemide, lodoxamide, tranilast, 21-phosphoric and 21-hemisuccinic esters of corticosteroids, sorbic acid, pirfenoxone, folic acid, fusidic acid, theophylline-acetic acid and bendazac.

44. The method of claim 34, wherein the therapeutically useful compound of a basic nature is selected from the group consisting of antihistamines, mucolytics, vasoconstrictors, β-blockers, antispasmodics, antiseptics, antitussives, basic anti-inflammatory drugs, bronchodilators, sympathicolytics, analgesics and antibiotics.

45. The method of claim 34, wherein the therapeutically useful compound of a basic nature is selected from the group consisting of chlorpheniramine, promethazine, azelastine, antazoline, cyproheptadine, tonzylamine, diphenydramine, emedastine, ketotifen, ambroxol, bromexine, naphazoline, tetryzoline, tramazoline, timolol, carteolol, ipratropium bromide, octylonium bromide, papaverine, rociverine, toripamide, chlorhexidine, benzalkonium chloride, benzetonium chloride, benzoxonium chloride, dequalinium chloride, codeine, oxolamine, dimemorfan, cloperastine, benzydamine, salbutamol, fenspiride, dapiprazole, chlorpromazine, prazosin, and lomefloxacin.

46. The method of claim 34, further comprising producing a powder, granule, tablet, freeze-dried product, or concentrate from said aqueous solution, wherein when said powder, granule, tablet, freeze-dried product, or concentrate is dissolved or diluted in an aqueous medium it produces a solution without a precipitate.

47. An aqueous composition comprising:
  a physiologically acceptable compound having an acidic nature,
  a physiologically acceptable compound having a basic nature, and a glycyrrhizic acid tricarboxylate salt,
  wherein the the physiologically acceptable compound having an acid nature and the physiologically acceptable compound having a basic nature are present at a ratio which gives rise to a precipitate in water and the glycyrrhizic acid tricarboxylate salt is present in a sufficient amount to form a clear solution.

48. The method of claim 1, wherein the quantity of said glycyrrhizic acid tricarboxylic salt ranges from 0.27 to 2.7% based on the weight of the solution.

49. The composition of claim 12, wherein the quantity of said glycyrrhizic acid tricarboxylic salt ranges from 0.27 to 2.7% based on the weight of the solution.

* * * * *